United States Patent [19]

Heissenberger et al.

[11] Patent Number: 4,464,796
[45] Date of Patent: Aug. 14, 1984

[54] GLOVE FORMED OF RUBBER OR PLASTICS MATERIAL AND MOLD FOR FABRICATING THE SAME

[75] Inventors: Oswald Heissenberger, Pottschach; Erwin Brandstätter, Neunkirchen, both of Austria

[73] Assignee: Semperit Aktiengesellschaft, Traiskirchen, Austria

[21] Appl. No.: 388,094

[22] Filed: Jun. 14, 1982

[30] Foreign Application Priority Data

Jun. 23, 1981 [AT] Austria .................................. 2766/81

[51] Int. Cl.³ ............................................ A41D 19/00
[52] U.S. Cl. .......................................... 2/168; 2/169; 2/162; 425/275; 223/78; 264/303
[58] Field of Search ................... 2/168, 169, 162, 167; 425/275, 369; 264/318, 303; 99/372, 382; 223/78

[56] References Cited

U.S. PATENT DOCUMENTS

| 3,268,647 | 8/1966 | Hayes et al. | 2/168 |
| 4,095,293 | 6/1978 | Heavner et al. | 2/168 |
| 4,133,624 | 1/1979 | Heavner et al. | 2/168 |

FOREIGN PATENT DOCUMENTS 208592 12/1907 Fed. Rep. of Germany ........ 99/372

Primary Examiner—Werner H. Schroeder
Assistant Examiner—Tracy G. Graveline
Attorney, Agent, or Firm—Werner W. Kleeman

[57] ABSTRACT

A glove formed of rubber or plastics material, especially an examination or surgical glove devoid of a roll-down preventing beaded edge and containing a structured surface at the cuff region. The structured surface is formed at the outer side or surface of the glove by non-connected raised portions, whereas the structured surface is formed at the inside or inner surface of the glove by mirror-image, non-connected recesses or depressions. The mold for fabricating the glove contains non-connected recesses at the cuff region.

3 Claims, 3 Drawing Figures

GLOVE FORMED OF RUBBER OR PLASTICS MATERIAL AND MOLD FOR FABRICATING THE SAME

BACKGROUND OF THE INVENTION

The present invention relates to a new and improved construction of glove formed of rubber or plastics material, especially an examination or surgical glove which is devoid of any roll-down preventing beaded edge and contains a structured surface at the cuff region of the glove. The invention further pertains to a novel construction of mold for the fabrication of such glove.

Some of the most important tasks or requirements assigned to an examination or surgical glove are that it firmly seat upon the hand of the user, does not unintentionally roll or slide down along the user's hand, particularly his or her wrist, and also, for instance, snugly encircles and holds down the cuff of the garment of the user. In the case of gloves which are provided with a roll-down preventing beaded edge at the cuff of the glove or with a strip-shaped reinforcement region, this fixation of the glove is to be accomplished particularly by the constriction of the coat arm around the user's wrist in that, at the garment cuff region there is formed a bead from the garment material which theoretically can not be overcome by the wrist portion of the glove.

However, during the course of the improved automation in the fabrication of examination or surgical gloves it was necessary to increasingly dispense with the use of an anti roll-down beaded edge and the complicated application of reinforcement strips. In the case of gloves which are fabricated at the present time without any anti roll-down beaded edge there exists the danger that such construction of glove will roll-down and so-to-speak flip over or upset in the direction of the hand portion, for instance during surgery. Due to the movements of the hand and the coat arm or sleeve such rolled-down cuff region, which now has its contaminated side facing towards the outside, tends to increasingly slide further in the direction of the hand portion. Consequently, not only does there occur an undesired exposure of the coat arm of the user, but also a contamination of the generally germ-free region, since the glove, as soon as it has been put on, is only free of germs at the outer surface. This becomes increasingly more problematic and dangerous since the sliding or rolling-down of the turned-over or upset region of the glove, under circumstances, can occur directly up to the region of the surface of the hand.

It is for these reasons that a glove which is fabricated without any anti roll-down beaded edge or without strip-like reinforcements is clearly more disadvantageous to use than a glove having a beaded edge serving for counteracting the glove roll-down problem, since the turning-over or upsetting of the wrist portion of a glove having a beaded edge can lead to roll-down of the wrist portion which, however, at the latest is terminated at the region of the user's wrist.

To prevent such problematic situation in the case of gloves which are devoid of any anti-roll beaded edge, attempts have already been made to obtain a rigidity of the cuff portion of the glove by imparting a particular configuration to such cuff portion, so that cuff roll-down is rendered more difficult. Thus, for instance, it has been proposed to arrange a plurality of elongated ribs over the circumference of the wrist portion of the glove which are supposed to prevent roll-down of the cuff portion because of their reinforcing action. However, the effect of such type of ribs was much too small, so that in this regard improvements are still being strived for. One such type of improved glove has been disclosed, for instance, in U.S. Pat. No. 4,133,624, granted Jan. 9, 1979.

In this U.S. Pat. No. 4,133,624 it has been proposed to solve the cuff roll-down problem in that, in addition to the reinforcement ribs arranged at the cuff region of the glove, there are also formed several ring-shaped ribs which constrict the wrist portion of the glove. The function of these ring-shaped ribs is similar to a beaded edge or a reinforcement band. There is rendered more difficult the rolling-down of the glove along the arm of the user.

However, this effect can only then arise if the elastomeric or rubber-elastic forces correspondingly tightly constrict the glove snugly about the coat arm of the user and hold such glove downwardly against the user's arm. However, an undesirable side effect which comes into play is the extremely uncomfortable pressure sensation which the doctor or other user of the glove experiences at the region of the lower arm or wrist portion. Additionally, by virtue of the coherent or continuous recesses which are present in the lengthwise direction at the inner surface of the glove there is again somewhat reduced the adherable contact or supporting surface of the glove upon the user's coat arm or sleeve, so that there is increased the possibility of roll-down of the glove along the coat arm. Thus, with this construction there still disadvantageously exists the problem of cuff roll-down of the glove and such is not adequately solved.

SUMMARY OF THE INVENTION

Therefore, with the foregoing in mind it is a primary object of the present invention to provide a new and improved construction of glove, especially for medical uses, which is not afflicted with the aforementioned drawbacks and limitations of the prior art proposals.

Another and more specific object of the present invention is directed to a new and improved construction of glove formed of rubber or a plastics material, particularly a glove which can be used as an examination or surgical glove, wherein there is imparted to such glove a structuring thereof at the cuff region, whereby there is effectively prevented cuff roll-down, turning-over or upsetting and sliding down of the glove along the coat arm or the wrist of the user, and additionally, such glove does not impart any uncomfortable feeling to the user during wearing thereof.

Still a further significant object of the present invention is directed to a new and improved construction of a medical or surgical glove having anti roll-down means which effectively prevent undesired cuff roll-down, and which glove is relatively simple in its construction and design, and quite economical to manufacture.

Yet a further significant object of the present invention is directed to a novel construction of mold for the fabrication of such type of glove.

Now in order to implement these and still further objects of the invention, which will become more readily apparent as the description proceeds, the glove of the present development is manifested by the features that, the structured surface at the outside of the glove is formed by non-coherent or non-continuous raised portions or protuberances, whereas at the inner surface of the glove such structured surface is formed of mirror-image, non-coherent or non-continuous recesses or depressions.

These nap-like non-continuous raised portions form, as soon as an attempt is made to roll-down the glove, a type of mutually interacting teeth which render impossible, or at the very least make extremely more difficult, a turning-over or upsetting, and thus, also roll-down of the cuff of the glove, since the roll-down radius which needs to be overcome for cuff roll-down or upsetting to occur now is so large that the elastomeric or rubber-elastic forces are no longer sufficient to overcome the same. Due to the non-continuous recesses at the inner surface of the glove there is simultaneously produced an increase in the static friction, so that there is appreciably rendered more difficult any sliding-out of the coat arm of the user from the wrist portion of the glove. In order to render the glove somewhat more resistant to the stresses exerted thereon when the glove is placed on the hand of the user, the wall thickness of the glove is selected to be somewhat larger at the region of the structured surface. Such differing wall thicknesses of the glove were heretofore not possible to attain, since during the dipping of the mold it was necessary to always immerse the entire glove, and thus, an increase in the wall thickness at the cuff region automatically also was associated with an increase of the wall thickness at the hand region or portion of the glove. However, due to the inventive design of the glove and its construction there is now automatically afforded for the first time the possibility, because of the reduced dripping capacity at the region of the structured surface or portion of the glove, to also select at that location the wall thickness to be somewhat greater than in comparison to the hand region or portion.

According to a further design of the invention the raised portions have a substantially pyramid-like configuration, so that there is optimumly realized the aforementioned tooth effect. Additionally, by virtue of the foregoing there is imparted to the glove at the cuff region a somewhat greater gripping capacity or traction, thus facilitating putting-on of the glove. The mirror-image recesses or depressions possess, corresponding to the raised portions, also substantially pyramid-like recesses depressions which bring about a good tooth-like meshing action with the fabric of the coat arm. Due to these teeth the frictional resistance is appreciably increased and there is markedly rendered more difficult any roll-down of the glove along the coat arm or wrist of the user.

In order to be able to fabricate a glove constructed according to the invention, it is contemplated, according to a further aspect of the present development, to use a mold having non-continuous recesses or depressions at the region of the cuff. The application of the rubber or the plastics material to this mold is accomplished, during the fabrication of the inventive glove, in accordance with conventional techniques.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
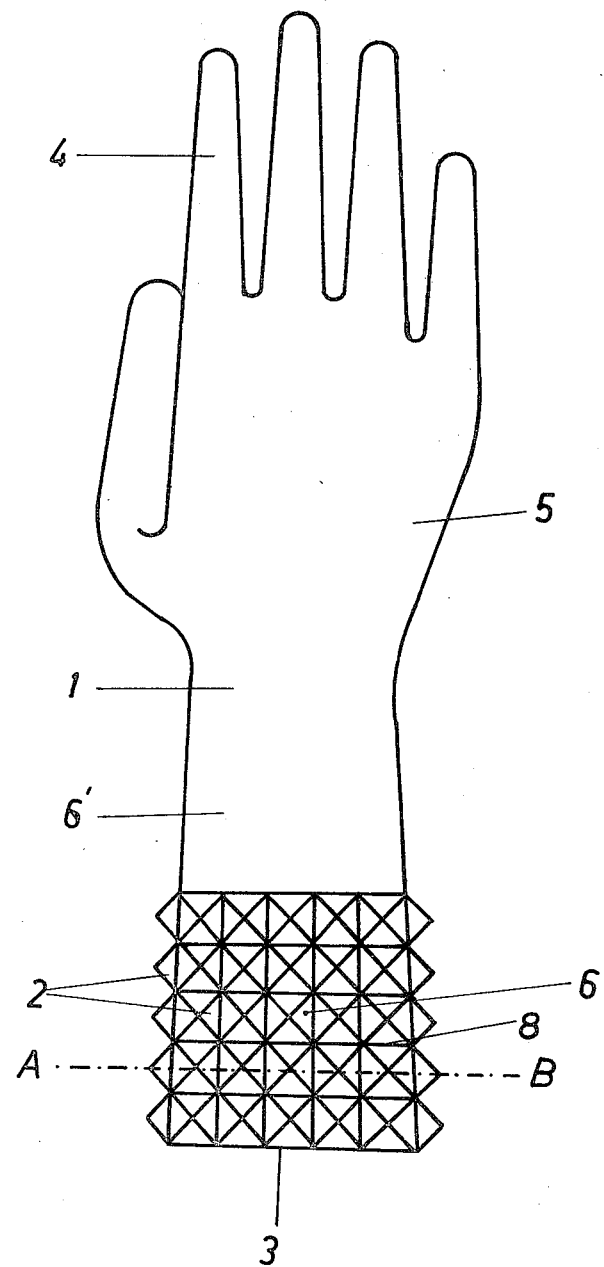
FIG. 1 schematically illustrates a glove constructed according to the invention and showing on an exaggerated scale the naps or protuberances at the wrist portion of such glove.

Turning attention now to the drawings it will be seen that the exemplary embodiment of glove 1 is divided into a finger portion or region 4, a hand portion or region 5, and a wrist portion or region 6' containing a cuff portion 6. The finger portion 4 and the hand portion 5 are constructed similar to conventionally known gloves. However, at the cuff portion or region 6 there are here formed substantially pyramid-shaped protuberances or raised portions 2 which impart to the glove 1, at this region, a nap-like appearance. As can be seen from FIGS. 1 and 2, a plurality of continuous circumferential bands 8 are formed at the inner surface of the glove between the substantially pyramid-like portions. The glove 1 does not contain any anti roll-down beaded edge at its cuff end 3. The pyramid-shaped raised portions 2 act like teeth, so that roll-down of the cuff portion or region 6 in the direction of the hand portion or region 5 is practically impossible. The pyramid-shaped raised portions 2 are provided at the inner surface of the glove with substantially pyramid-shaped recesses or depressions 7 having the same surface area, as such will be apparent from the illustration of FIG. 2. It is here once again mentioned that the pyramid-like raised portions 2 and the recesses 7 have been illustrated on an exaggerated scale in order to render clearer the teachings of the invention and the function thereof and, in practical applications, only possess a height of approximately 1 mm.

Figure 2:
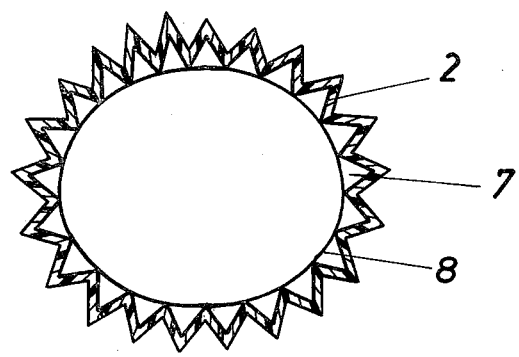
FIG. 2 is a cross-sectional view of the glove shown in FIG. 1, the section being taken through the wrist portion of the glove substantially along the section line A-B of FIG. 1.
Figure 3:
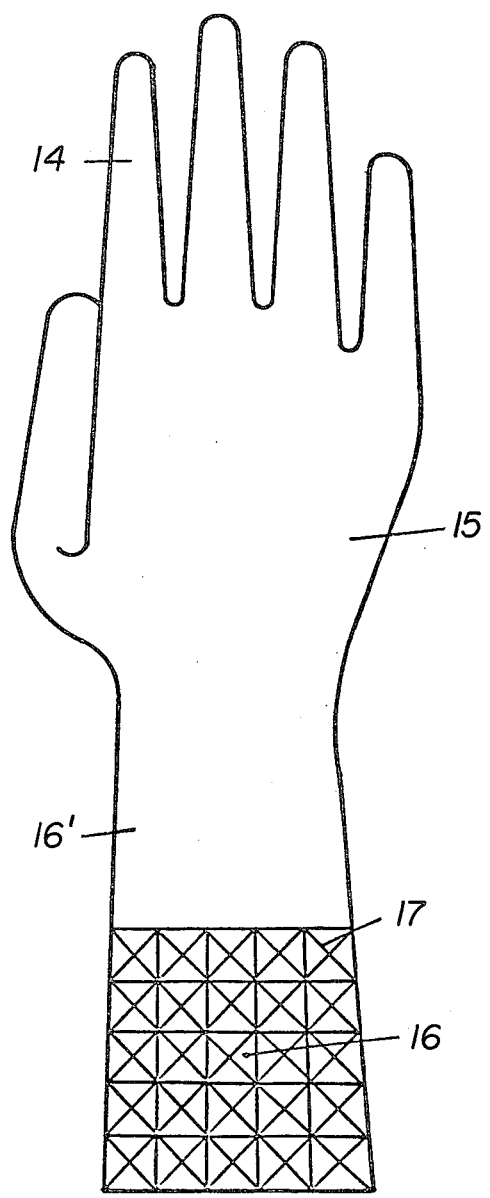
FIG. 3 is a top plan view of a mold according to the invention for preparing the glove as shown in FIG. 1.

In FIG. 3 there is shown a top plan view of the mold for preparing the glove as described hereinbefore. The mold comprises a finger mold portion or region 14, a hand mold portion or region 15, and a wrist mold portion or region 16' containing a cuff mold portion or region 16. In the cuff mold portion or region 16 there are formed substantially pyramid-shaped recesses or depressions 17. In forming the glove, the mold is dipped in conventional manner into the respectively desired latex composition such that a surface layer of the latex composition adheres to the surface of the mold. After vulcanization of the latex composition on the mold and drying, the product is removed from the mold and turned inside out to produce the glove as shown in FIGS. 1 and 2.

Finally, it is mentioned that the underlying principles and concepts of the invention encompass any other type of non-continuous or non-coherent raised portions at the wrist portion of the glove at the region of the cuff, such as, for instance, segmented spherical-shaped raised portions, even if such have not been specifically heretofore mentioned in the foregoing disclosure.

While there are shown and described present preferred embodiments of the invention, it is to be distinctly understood that the invention is not limited thereto, but may be otherwise variously embodied and practiced within the scope of the following claims. Accordingly,

What we claim is:

1. A glove formed of rubber or plastics material, especially an examination or surgical glove devoid of any anti roll-down beaded edge, said glove comprising:
a finger portion, hand portion and wrist portion; said wrist portion including a cuff region; and a structured surface provided at the cuff region; said structured surface being constituted at the outer surface of the glove by non-continuous raised substantially pyramid-like portions and at the inner surface of the glove by substantially complementary, non-continuous substantially pyramid-like recesses wherein a plurality of continuous circumferential bands are formed at the inner surface between said portions whereby the anti roll-down beaded edge can be eliminated.

2. The glove as defined in claim 1, wherein:
the thickness of the material of the glove at the region of the structured surface is somewhat greater than at the region of the hand portion.

3. A mold for the fabrication of a glove formed of rubber or plastics material, especially an examination or surgical glove having a finger portion, a hand portion, and a wrist portion devoid of any anti roll-down beaded edge, said mold containing a finger portion, hand portion and wrist portion, said wrist portion including a cuff region, a structured surface provided at the cuff region, said structured surface being constituted so as to form at the outer surface of the wrist portion of the glove non-continuous raised substantially pyramid-like portions and at the inner surface of the glove substantially complementary, non-continuous substantially pyramid-like recesses and a plurality of continuous circumferential bands between said portions, the improvement wherein:
the mold at the region of the cuff possesses non-continuous substantially pyramid-like recesses and a plurality of continuous ridges between said recesses.

* * * * *